United States Patent
Lim et al.

(10) Patent No.: US 9,541,375 B2
(45) Date of Patent: Jan. 10, 2017

(54) METHOD AND APPARATUS FOR GENERATING TOMOGRAPHY IMAGES

(71) Applicants: Samsung Electronics Co., Ltd., Suwon-si (KR); Korea Advanced Institute Of Science and Technology, Daejeon (KR)

(72) Inventors: Jae-guyn Lim, Seongnam-si (KR); YongKeun Park, Daejeon (KR); Jae-duck Jang, Daejeon (KR); Hyeon-seung Yu, Daejeon (KR); Seong-deok Lee, Seongnam-si (KR); Woo-young Jang, Seongnam-si (KR)

(73) Assignees: Samsung Electronics Co., Ltd., Suwon-si (KR); Korea Advanced Institute of Science and Techonlogy, Daejeon (KR)

( * ) Notice: Subject to any disclaimer, the term of this patent is extended or adjusted under 35 U.S.C. 154(b) by 364 days.

(21) Appl. No.: 13/946,240

(22) Filed: Jul. 19, 2013

(65) Prior Publication Data
US 2014/0022554 A1    Jan. 23, 2014

Related U.S. Application Data

(60) Provisional application No. 61/674,051, filed on Jul. 20, 2012.

(30) Foreign Application Priority Data

Nov. 27, 2012  (KR) ........................ 10-2012-0135556

(51) Int. Cl.
*G01B 11/02*   (2006.01)
*G01B 9/02*    (2006.01)
*G01N 21/17*   (2006.01)

(52) U.S. Cl.
CPC ......... *G01B 9/02091* (2013.01); *G01B 9/0201* (2013.01); *G01B 9/02083* (2013.01); *G01N 2021/1787* (2013.01)

(58) Field of Classification Search
CPC . G01B 9/02091; G01B 9/0209; G01B 9/0201; G01B 9/02083; G01N 2021/1787
(Continued)

(56) References Cited

U.S. PATENT DOCUMENTS 7,460,248 B2   12/2008  Kurtz et al.
7,920,271 B2    4/2011  Vakoc et al.
(Continued)

FOREIGN PATENT DOCUMENTS

EP   2 314 202 A1   4/2011
EP   2 314 203 A1   4/2011
(Continued)

OTHER PUBLICATIONS

Vellekoop, I. M., et al. "Phase control algorithms for focusing light through turbid media." Optics Communications 281.11 (2008): 3071-3080.
(Continued)

*Primary Examiner* — Tarifur Chowdhury
*Assistant Examiner* — Jonathon Cook
(74) *Attorney, Agent, or Firm* — NSIP Law

(57) ABSTRACT

A method and apparatus are provided to generate tomography images that performs the method. The apparatus and method are configured to determine a basis pattern from modulated phases of incident rays from a spatial light modulator according to a pattern of arranged pixels. The apparatus and method are further configured to perform spatial shift modulation shifting an arrangement of the pixels vertically or horizontally with respect to the basis pattern to obtain shift patterns of the basis pattern. The apparatus and
(Continued)

method are configured to generate tomography images for the basis pattern and the shift patterns using spectrum signals of rays obtained from the incident rays passing through the spatial light modulator and entering a subject. The apparatus and method are configured to select a pattern that generates a clearest tomography image of the subject based on the generated tomography images.

13 Claims, 8 Drawing Sheets

(58) Field of Classification Search
USPC .................................................. 356/479, 497
See application file for complete search history.

(56) References Cited

U.S. PATENT DOCUMENTS

| 2003/0234938 | A1* | 12/2003 | Ge ..................... G01B 9/0201 356/497 |
|---|---|---|---|
| 2006/0227333 | A1 | 10/2006 | Tearney et al. |
| 2007/0081236 | A1 | 4/2007 | Tearney et al. |
| 2007/0201033 | A1 | 8/2007 | Desjardins et al. |
| 2007/0233396 | A1 | 10/2007 | Tearney et al. |
| 2008/0002211 | A1 | 1/2008 | Park et al. |
| 2009/0128824 | A1 | 5/2009 | Leitgeb et al. |
| 2011/0102741 | A1 | 5/2011 | Hirose |
| 2011/0122416 | A1* | 5/2011 | Yang .................. G02B 21/0056 356/457 |

FOREIGN PATENT DOCUMENTS

| EP | 2 465 414 A1 | 6/2012 |
|---|---|---|
| KR | 10-2012-0060746 A | 6/2012 |
| WO | WO 2010/004297 A1 | 1/2010 |

OTHER PUBLICATIONS

Extended European Search Report issued Dec. 5, 2013 in counterpart European Application No. 13177431.7.

* cited by examiner

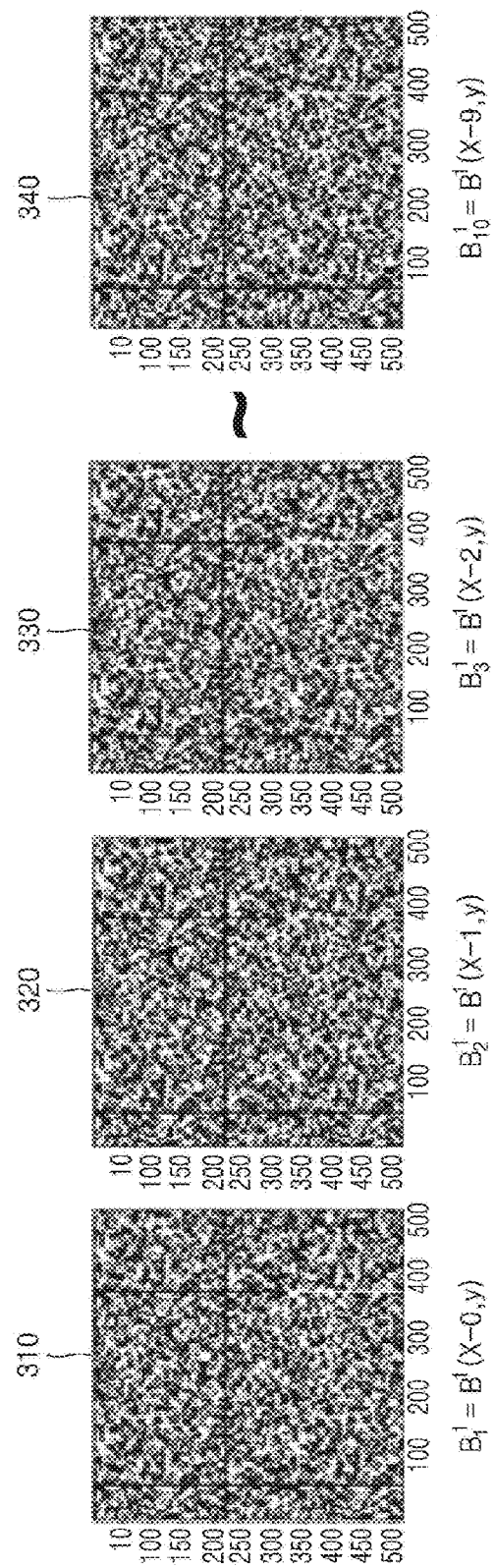

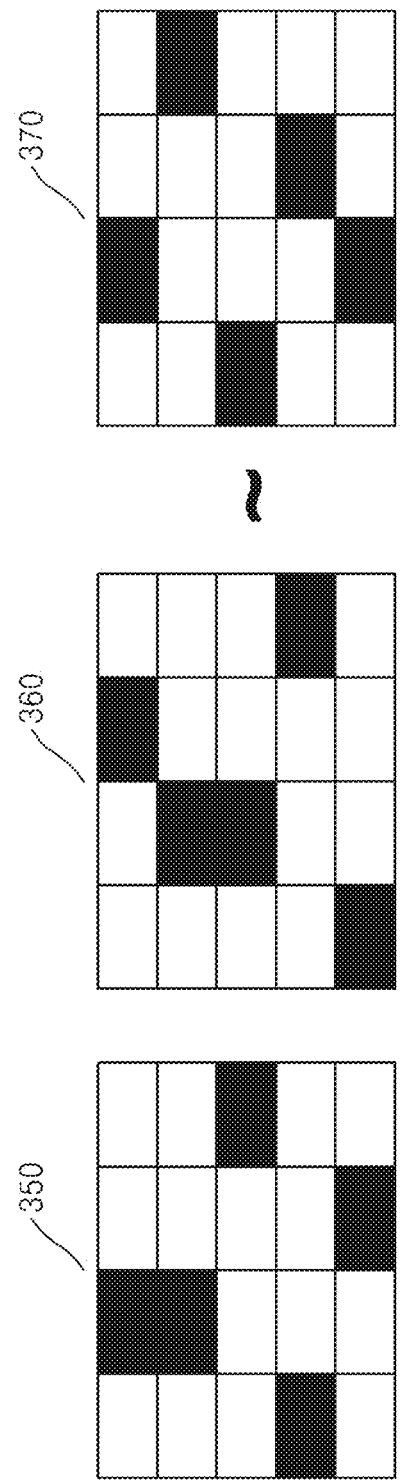

METHOD AND APPARATUS FOR GENERATING TOMOGRAPHY IMAGES

CROSS-REFERENCE TO RELATED APPLICATION(S)

This application claims the benefit of U.S. Provisional Application No. 61/674,051, filed on Jul. 20, 2012, in the U.S. Patent and Trademark Office and Korean Patent Application No. 10-2012-0135556, filed on Nov. 27, 2012, in the Korean Intellectual Property Office, the disclosures of which are incorporated herein in their entirety by reference.

BACKGROUND

1. Field

The present disclosure relates to methods and apparatuses to generate tomography images using light.

2. Description of the Related Art

Light is being currently used in various technical fields with optical characteristics that include monochromaticity, coherence, and directionality. In the biological and medical fields, the light is utilized to observe tissues or cells, diagnosing disease, or performing laser surgery in various ways.

Using the optical characteristic of light, it is possible to capture high resolution images of living tissues or cells and to observe internal organs and structures of human bodies and living bodies without cutting them. The captured high resolution images may be utilized to easily and safely recognize the cause, position, and progress of various kinds of diseases in the medical field. When capturing tomography images of human bodies or living bodies using light, a transmission depth of light may be necessarily increased to transmit the light to cells or tissues in the deep position of human bodies or living bodies.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In accordance with an illustrative example, there is provided a method to generate a tomography image, the method including: determining a basis pattern from modulated phases of incident rays from a spatial light modulator according to a pattern of arranged pixels; performing spatial shift modulation shifting an arrangement of the pixels vertically or horizontally with respect to the basis pattern to obtain shift patterns of the basis pattern; generating tomography images for the basis pattern and the shift patterns using spectrum signals of rays obtained from the incident rays passing through the spatial light modulator and entering a subject; and selecting a pattern that generates a clearest tomography image of the subject based on the generated tomography images.

The method also includes configuring the spatial light modulator to comprise basis patterns for the subject, wherein the basis patterns are uncorrelated with each other in phase modulation of the incident rays according to the spatial shift modulation.

The method further includes generating a final tomography image for the subject using the selected pattern; and configuring the spatial light modulator to comprise basis patterns of the subject, wherein the selecting of the one pattern includes obtaining selected patterns by repeating, for each of the basis patterns, the selecting of one pattern that generates the clearest tomography image among each basis pattern and the shift patterns; summing the selected patterns as one summation pattern; and forming a final pattern obtained by binarizing the summation pattern based on a predetermined threshold, and wherein the generating of the final tomography image includes generating the final tomography image for the subject using the final pattern.

The method also includes generating a final tomography image for the subject using the selected pattern; and determining a region of interest (ROI) that corresponds to a desired transmission depth of the subject to focus the incident rays, wherein the determining of the basis pattern, the performing, the generating, and the selecting are repeated for the ROI to generate the final tomography image for the ROI.

The method further includes determining region of interests (ROIs) that have different transmission depths of the subject to focus the incident rays, wherein the determining of the basis pattern, the performing, the generating, and the selecting are repeated each for the ROIs to generate final tomography images, and the final tomography images are combined to generate one edited tomography image.

The determining of the ROI includes determining the desired transmission depth of the subject to focus the incident rays based on an intensity of the spectrum signals according to transmission depth of the subject, and determining a region corresponding to the determined transmission depth as the ROI.

The method includes obtaining spectrum images, each for each of the basis pattern and the shift patterns for each of the basis pattern based on the spectrum signals; and generating one phase shift spectrum image representing phase shift of the obtained rays according to the spatial shift modulation by arranging, in a matrix form, the spectrum images according to a shift direction and a shift amount of the spatial shift modulation based on a spectrum image of the basis pattern, The obtaining of the spectrum images and the generating of the one phase shift spectrum image are repeated for the basis patterns to obtain phase shift spectrum images. The generating of the final pattern includes generating the final pattern by the selecting of one pattern that generates the clearest tomography image, on basis patterns of phase shift spectrum images that have regular phase shift among the phase shift spectrum images.

The method includes representing the regular phase shift with sinusoidal characteristics.

While horizontally moving the incident rays on the subject, the determining of the basis pattern, the performing, the generating, and the selecting repeated to obtain final tomography images, and the method further including generating a tomography image of a region that corresponds to an entire moving distance on the subject using the final tomography images.

The method further includes configuring the spatial light modulator to be a digital micro-mirror device (DMD).

The method also includes determining the basis patterns based on a permutation of a Hadamard pattern.

The method includes performing the determining, the performing, the generating, and the selecting at an optical coherent tomography (OCT) apparatus or an optical coherent microscopy (OCM).

In accordance with an illustrative example, there is provided a computer program embodied on a computer readable medium, the computer program being configured to control a processor to perform the method of claim 1.

In accordance with another illustrative example, there is provided a tomography image generating apparatus, including: a spatial light modulator configured to modulate a phase of incident rays upon a subject according to a pattern of arranged pixels; a modulation controller configured to determine a basis pattern, to perform spatial shift modulation shifting an arrangement of pixels vertically or horizontally with respect to the basis pattern to obtain shift patterns of the basis pattern, and to control the spatial light modulator to sequentially apply each of the basis pattern and the shift patterns; a detector configured to detect spectrum signals for the basis pattern and the shift patterns based on rays obtained from the incident rays that pass through the spatial light modulator and enter the subject; an image generator configured to generate tomography images of the basis pattern and the shift patterns using the spectrum signals; and an image processor configured to select a pattern that generates a clearest tomography image among the basis pattern and the shift patterns based on the generated tomography images.

The image generator generates a final tomography image of the subject using spectrum signals of the rays obtained by applying the selected pattern to the spatial light modulator.

The modulation controller is further configured to determine basis patterns for the subject and to perform the spatial shift modulation on each of the basis patterns to obtain shift patterns for each basis pattern, and wherein the basis patterns are uncorrelated with each other in the phase modulation of the incident rays, according to the spatial shift modulation.

The modulation controller is further configured to determine basis patterns for the subject, to perform the spatial shift modulation on each of the basis patterns to obtain shift patterns for each basis pattern, and to sequentially apply the basis patterns and the shift patterns for each basis pattern to the spatial light modulator, the image processor is further configured to obtain selected patterns by repeating an operation of the selecting, for each of the basis patterns, to sum the selected patterns as a summation pattern, and to form a final pattern obtained by binarizing the summation pattern on a predetermined threshold, and wherein the image generator is further configured to use the final pattern to generate the final tomography image for the subject.

The apparatus also includes a light controller configured to determine a region of interest (ROI) corresponding to a desired transmission depth of the subject to focus the incident rays and to control the emitting to enable the incident rays to be focused on the determined ROI, wherein the light controller is further configured to determine regions of interest (ROIs) including different transmission depths of the subject to focus the incident rays, and to control the emitting to enable the incident rays to be sequentially focused on the ROIs, the image generator is further configured to repeat the generating of the final tomography image for the ROIs of the subject to obtain final tomography images, and the image processor is further configured to combine the final tomography images to generate one edited tomography image.

The image generator obtains spectrum images each for the each basis pattern and shift patterns for the each basis pattern based on the spectrum signals, the image processor is further configured to arrange the spectrum images in matrix form according to shift direction and shift amount of the spatial shift modulation on a basis of a spectrum image of the each basis pattern, and to generate a phase shift spectrum image that represents phase shift of the obtained rays according to spatial shift modulation, the image processor is further configured to repeat the generating of the one phase shift spectrum image for each of the basis patterns to obtain phase shift spectrum images, and to perform the selecting of one pattern that generates a clearest tomography image on basis patterns of phase shift spectrum images that show regular phase shift among the phase shift spectrum images.

The regular phase shift represents sinusoidal characteristics.

In accordance with another illustrative example, there is provided an optical coherence tomography apparatus, including: a spatial light modulator configured to modulate a phase of incident rays upon a subject according to a pattern of arranged pixels; controller configured to determine a basis pattern, to perform spatial shift modulation shifting an arrangement of pixels vertically or horizontally with respect to the basis pattern to obtain shift patterns of the basis pattern, and to control the spatial light modulator to sequentially apply each of the basis pattern and the shift patterns; an interferometer configured to split the incident rays into measuring rays and reference rays, irradiating the measuring rays to the subject, and receiving response rays reflected from the subject; a detector configured to detect interference signals caused by the response rays and the reference rays, and to detect spectrum signals for each of the basis pattern and shift patterns based on the interference signals; an image generator configured to generate tomography images for the basis pattern and the shift patterns using the spectrum signals; and an image processor configured to select a pattern that generates a clearest tomography image among the basis pattern and the shift patterns based on the generated tomography images.

The image generator generates a final tomography image of the subject using spectrum signals of the interference signals obtained by applying the selected pattern to the spatial light modulator.

The spatial light modulator modulates a phase of at least one of the incident rays emitted from a light emitter emitting the rays incident upon the subject, the measuring rays or the reference rays.

BRIEF DESCRIPTION OF THE DRAWINGS

These and/or other aspects will become apparent and more readily appreciated from the following description of the embodiments, taken in conjunction with the accompanying drawings of which:

FIG. 3A is illustrating an example of shift patterns obtained from a modulation controller in FIG. 1 performing spatial shift modulation on a basis pattern, according to an embodiment;

FIG. 3B is illustrating an example of operations to obtain the plurality of shift patterns from the modulation controller in FIG. 1 performing spatial shift modulation on the basis pattern, according to an embodiment;

DETAILED DESCRIPTION

The following detailed description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, description of well-known functions and constructions may be omitted for increased clarity and conciseness.

The terminology used herein is for the purpose of describing particular embodiments only and is not intended to be limiting of the present invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which the present invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Example embodiments are described herein with reference to sectional illustrations that are schematic illustrations of idealized embodiments (and intermediate structures) of the present invention. As such, variations from the shapes of the illustrations as a result, for example, of manufacturing techniques and/or tolerances, are to be expected. Thus, example embodiments of the present invention should not be construed as limited to the particular shapes of regions illustrated herein but are to include deviations in shapes that result, for example, from manufacturing. The regions illustrated in the figures are schematic in nature and their shapes are not intended to illustrate the actual shape of a region of a device and are not intended to limit the scope of the present configurations. Exemplary embodiments will be described in detail below with reference to the drawings.

Figure 1:
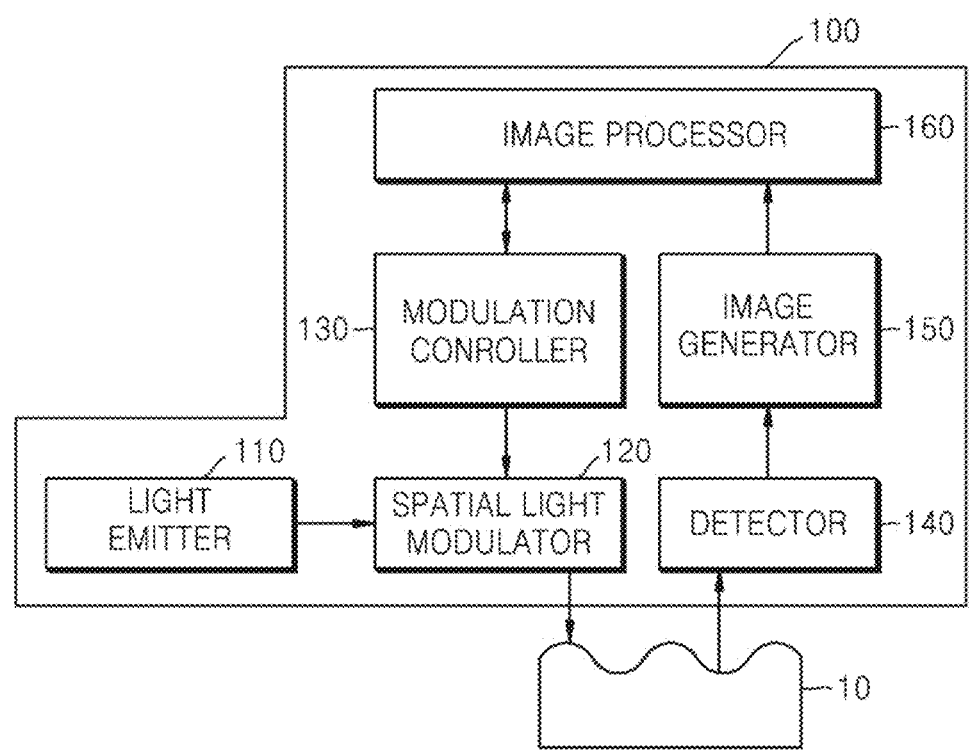
FIG. 1 is a block diagram illustrating an apparatus to generate tomography images, according to an embodiment.

FIG. 1 is a block diagram illustrating an apparatus to generate tomography images, according to an embodiment. Referring to FIG. 1, the tomography image generating apparatus 100 includes a light emitter 110, a spatial light modulator 120, a modulation controller 130, a detector 140, an image generator 150, and an image processor 160.

The tomography image generating apparatus 100, according to the illustrative example shown in FIG. 1, is a structural apparatus to obtain the tomography images of a subject using light and includes optical image apparatuses that may obtain tomography images using optical coherence, such as an optical coherence tomography (OCT) apparatus, an optical coherent microscopy (OCM), and an optical microscope. In one example, the subject may be a person, an animal, an organ, or similar organism.

The light emitter 110 emits rays to be incident upon a subject 10. For example, the light emitter 110 may emit wavelength-swept light, laser, or other similar or different types of beams, but is not limited thereto. The rays emitted from the light emitter 110 enter the subject 10 via the spatial light modulator 120.

The spatial light modulator 120 modulates phases of incident rays according to a pattern in which pixels are arranged. For example, the spatial light modulator 120 may be a digital micro-mirror device (DMD), but is not limited thereto. Illustrative descriptions of phase modulation of the spatial light modulator 120 are made with respect to FIGS. 2A and 2B.

The modulation controller 130 determines at least one basis pattern from the modulated phases of incident rays from the spatial light modulator 120 and performs spatial shift modulation on the at least one basis pattern to obtain shift patterns of the basis pattern. In one configuration, the at least one basis pattern represents a reference pattern from which to perform spatial shift modulation. In an example, the spatial shift modulation shifts arrangement of the pixels vertically or horizontally by a predetermined number with respect to one basis pattern to obtain a shift pattern.

The modulation controller 130 controls the spatial light modulator 120 so that each of the basis pattern and the shift patterns is sequentially applied to the spatial light modulator 120. The modulation controller 130 may obtain shift patterns with respect to one basis pattern. The detailed descriptions of the spatial shift modulation of the modulation controller 130 are presented in the description associated with FIGS. 3A and 3B.

The detector 140 detects spectrum signals based on rays obtained from incident rays entering the subject 10 from the spatial light modulator 120. The obtained rays may be obtained through a phenomenon including, but not limited to, transmission, reflection, and scattering when the incident rays enter the subject 10 through the spatial light modulator 120. For example, the obtained rays may be obtained through an interference phenomenon between a reference ray and a response ray obtained from the measuring rays entering the subject 10. As another example, the obtained rays may be obtained through an interference phenomenon between secondary harmonic signals of each of the response ray and the reference ray. Other similar processes may be implemented to obtain the obtained rays.

The image generator 150 generates tomography images based on the basis pattern and the shift patterns. For example, the modulation controller 130 applies the basis pattern to the spatial light modulator 120, the detector 140 detects a spectrum signal for the applied basis pattern, and the image generator 150 generates a tomography image based on the spectrum signal of the basis pattern. In addition, the modulation controller 130 applies a first shift pattern, which is formed through vertical or horizontal spatial shift modulation of the basis pattern, to the spatial light modulator 120. The detector 140 detects a spectrum signal for the first shift pattern, and the image generator 150 generates a tomography image based on the spectrum signal of the first shift pattern. Likewise, the modulation controller 130 obtains shift patterns, such as a second shift pattern, a third shift pattern, etc., which are formed through the spatial shift modulation of the basis pattern, with a shift direction and a shift amount different from those of the first shift pattern. The image generator 150 obtains tomography images for the second shift pattern, the third shift pattern, and additional shift patterns, if any, based on spectrum signals that are obtained by sequentially applying the shift patterns.

The image processor 160 selects one pattern that generates a clearest tomography image among the basic pattern and the shift patterns of the basis pattern. For example, the clearest tomography image is one that allows all the rays that enter the subject 10 to be in-phase. If all the rays that enter the subject 10 are in-phase, the in-phase rays focus on one point of the subject 10 and the energy of the rays is maximized. Thus, the clearest tomography image is represented when the energy of light from obtained tomography images is maximized, and indicates a tomography image with the greatest light intensity among the obtained tomography images. In one illustrative example, the clearest tomography image is represented by the energy of light from the brightest tomography image. The image processor 160 selects one pattern that corresponds to the tomography image selected as the clearest tomography image among the shift patterns of the basis pattern. For example, the operations to determine one pattern generating the clearest tomography image by the image processor 160 may be automatically performed by a processor, a controller, a computer program stored in a non-transitory computer readable medium, or other similar devices.

The image processor 160, according to an illustrative configuration, corresponds to or includes at least one processor or controller. In addition, the image processor 160 may be located in the tomography image generating apparatus 100 as illustrated in FIG. 1 but may be located separately from the tomography image generating apparatus 100.

The image generator 150 generates a final tomography image of the subject 10 using a spectrum signal detected by applying the selected pattern to the spatial light modulator 120.

According to an embodiment, the tomography image generating apparatus 100 may use basis patterns. The basis patterns modulate the phase of each of rays entering the subject 10 to generate the final tomography image optimized for the subject 10.

According to this embodiment, the modulation controller 130 determines basis patterns for the subject 10 and obtains shift patterns each for the basis patterns. In this example, the modulation controller 130 determines basis patterns so that the basis patterns are uncorrelated to each other during phase modulation of the incident rays in accord with the spatial shift modulation. As an embodiment, the modulation controller 130 determines basis patterns so that the basis patterns have an orthogonal relation with each other. In addition, the basis patterns that have uncorrelated relation may be determined based on a permutation of, for instance, a Hadamard pattern.

The modulation controller 130 performs spatial shift modulation on each basis pattern to obtain shift patterns for each basis pattern. The modulation controller 130 sequentially applies the basis patterns and the shift patterns for each basis pattern to the spatial light modulator 120 to generate tomography images. According to the pattern applied to the spatial light modulator 120, the image generator 150 generates tomography images for the basis patterns and the shift patterns for each basis pattern.

The image processor 160 repeats the operation to select one pattern that generates a clearest tomography image among each basis pattern and the shift patterns for each basis pattern to obtain a plurality of selected patterns. The selected patterns correspond to a set of patterns that optimally modulates the phases of the incident rays entering the subject 10 according to material characteristics of the subject 10. In order to determine one pattern with an optimal phase modulation amount, the image processor 160 sums the selected patterns as one summation pattern. In order to apply the summation pattern to the spatial light modulator 120, the image processor 160 binarizes the summation pattern based on a predetermined threshold and forms a binarized final pattern. The modulation controller 130 applies the final pattern to the spatial light modulator 120. The image generator 150 generates the final tomography image for the subject using the final pattern as described above. The final tomography image corresponds to a tomography image with a phase that is modulated and optimized according to the material characteristics of the subject 10.

According to an embodiment, the tomography image generating apparatus 100 may generate the final pattern using some basis patterns that show regular phase shift among the basis patterns. The image processor 160 generates one phase shift spectrum image using the spectrum images of a basis pattern and shift patterns for the basic pattern. The phase shift spectrum image represents phase shift of the obtained rays according to the spatial shift modulation. The image processor 160 generates phase shift spectrum images for the basic patterns.

According to this embodiment, the image generator 150 may obtain the spectrum images for one basis pattern and shift patterns of the basis pattern based on spectrum signals. The image processor 160 arranges the spectrum images of the shift patterns of the basis pattern in matrix form according to shift direction and shift amount of the spatial shift modulation on the basis of a spectrum image of the basis pattern. The image processor 160 generates one phase shift spectrum image from the basis pattern.

The image processor 160 repeats the operation to generate one phase shift spectrum image for each of the basis patterns to obtain the phase shift spectrum images.

In one illustrative example, the image processor 160 uses basis patterns of the phase shift spectrum images that show regular phase shift among the phase shift spectrum images and the shift patterns of the basis pattern of the phase shift spectrum images, for generating the final pattern. Thus, the image processor 160 selects one pattern that generates a clearest tomography image, on the basis patterns of the phase shift spectrum images that show regular phase shift and the shift patterns of the basis pattern of the phase shift spectrum images. The image processor 160 generates the final pattern using the selected patterns through the selection operation.

In one example, the regular phase shift is a phase shift amount according to spatial shift modulation changes with certain regularity. For example, if the phase shift represented in a phase shift spectrum image has sinusoidal characteristics, it may be determined that there is a regular phase shift. In this case, the operation that the image processor 160 determines whether a phase shift spectrum image has regular phase shift may be automatically performed by a processor, a controller, a computer program stored in a non-transitory computer readable medium, or other similar devices.

The tomography image generating apparatus 100, according to an embodiment, may further include a light controller (not illustrated). The light controller (not illustrated) determines a region of interest (ROI) that corresponds to a desired transmission depth of the subject 10 for rays to be focused on, and controls the rays to be focused on the determined ROI. The image generator 150 generates the final tomography image using the final pattern obtained by obtaining the final pattern with the optimal phase modulation amount on the determined ROI of the subject 10.

The light controller (not illustrated) may determine ROIs that have different transmission depth of the subject 10 upon which rays are to be focused. Thus, the light controller (not illustrated) controls the rays to be sequentially focused on the ROIs. The image generator 150 generates the final tomography image sequentially for the ROIs to obtain final tomography images. The image processor 160 connects the final tomography images to generate one edited tomography image. Thus, the tomography image generating apparatus 100 connects the final tomography images optimized for each transmission depth to obtain one tomography image corresponding to an entire transmission depth.

According to an embodiment, the optical controller (not illustrated) determines the transmission depth of the subject 10 upon which rays are focused on based on an intensity of spectrum signals according to the transmission depth of the subject 10. The optical controller (not illustrated) may also determine a region corresponding to the determined transmission depth as an ROI. For example, the image generator 150 uses spectrum signals with the highest intensity as a basis pattern and shift patterns as the basis pattern to generate tomography images. As the transmission depth of the subject 10 increases, the intensity of a spectrum signal gradually decreases. Thus, the tomography image generating apparatus 100 may obtain tomography images with a certain transmission depth by generating tomography images based on spectrum signals with the highest intensity. A processor, a controller, a computer program stored in a non-transitory computer readable medium, or other similar devices may automatically perform a determination of the transmission depth of the subject 10, on which rays are focused, based on the intensity of spectrum signals.

In addition, the optical controller (not illustrated) may horizontally move the position of the subject 10 which rays enter. As the position of the rays moves, the image generator 150 sequentially obtains final tomography images that correspond to the position of each of the moving rays. The image processor 160 connects the final tomography images to generate one tomography image of a region that corresponds to the entire moving distance on the subject 10. Thus, the tomography image generating apparatus 100 may combine optimal tomography images optimized for the position moved by the optical controller (not illustrated) to obtain one tomography image corresponding to the entire horizontal moving distance.

Figure 2A:
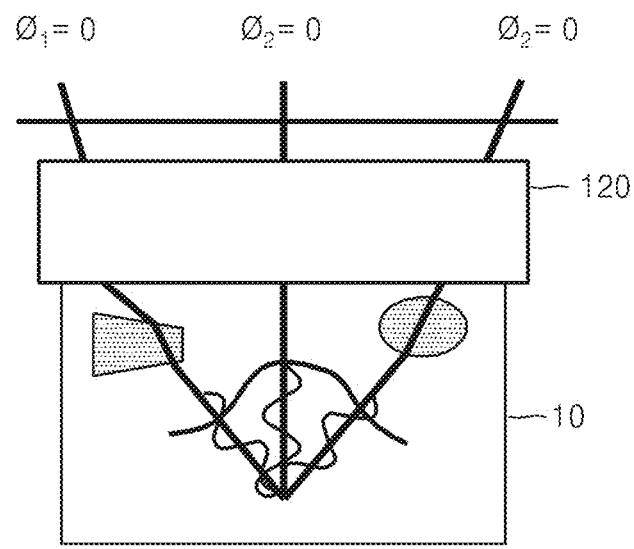
FIG. 2A is an illustration showing rays transmitted and focused on a subject, where the rays are not modulated by a spatial light modulator, according to an embodiment.

FIG. 2A is an illustration showing rays transmitted and focused on a subject, where the rays are not modulated by a spatial light modulator, according to an embodiment.

Referring to FIG. 2A, the rays to be focused inside the subject 10 are emitted from the light emitter 110. The phase modulation amount of each ray is represented as $\phi 1$, $\phi 2$, and $\phi 3$. The phase modulation amount of the rays of FIG. 2A is 0 and the rays are ones with phases that have not been modulated by the spatial light modulator 120. The rays emitted from the light emitter 110 enter the subject 10. In this case, the material characteristic of the subject 10 for which a tomography image is generated is non-uniform and turbid. Thus, while the rays are in phase before entering the subject 10, the phase of each of the rays changes due to the material characteristic of the subject 10. Thus, the rays are not in phase at a point in which a tomography image is to obtained, at a focus point. Also, as the rays are not in phase at the focus point, the focused energy of these rays decreases compared to a case in which the rays would be in phase.

Figure 2B:
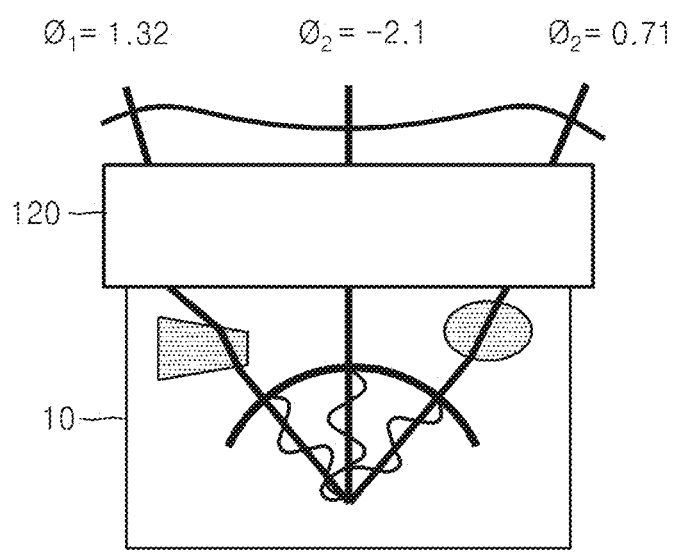
FIG. 2B is an illustration showing rays transmitted and focused on a subject, where the rays are modulated by the spatial light modulator illustrated in FIG. 1, according to an embodiment.

FIG. 2B is an illustration showing rays transmitted and focused on a subject, where the rays are modulated by the spatial light modulator illustrated in FIG. 1, according to an embodiment. The rays emitted from the light emitter 110 enter the spatial light modulator 120 of FIG. 2B and are focused inside the subject 10. Like FIG. 2A, the material characteristic of the subject 10 for which a tomography image will be generated is non-uniform and turbid.

The phases of the rays of FIG. 2B are modulated by the spatial light modulator 120 and the modulated rays are transmitted to the subject 10. The phase modulation amount of each ray illustrated in FIG. 2B is represented as $\phi 1=1.32$, $\phi 2=-2.1$, and $\phi 3=0.71$. The phases of the rays of FIG. 2B are modulated to be different from one another by the spatial light modulator 120. While the rays are out of phase before entering the subject 10, the rays are in-phase at a focus point for which a tomography image will be obtained, and as a result, the focused energy of the rays is maximized.

In order to maximize the focused energy of the rays that enter the non-uniform and turbid subject 10, the tomography image generating apparatus 100, according to the present embodiment, utilizes spatial shift modulation to control the phase modulation amount of each of the rays.

The tomography image generating apparatus 100, according to an illustrative example, selects a pattern that generates the clearest tomography image among a basis pattern and shift patterns of the basis pattern obtained using spatial shift modulation, and may, thus, generate an optimal tomography image using the selected pattern. The selected pattern represents a phase modulation amount most suitable for the material characteristic of a corresponding subject 10.

FIG. 3A is illustrating an example of a plurality of shift patterns obtained from a modulation controller in FIG. 1 performing spatial shift modulation on a basis pattern, according to an embodiment. The patterns illustrated FIG. 3A represent shift patterns that are obtained by shifting the arrangement of pixels horizontally one by one based on the basis pattern.

The modulation controller 130 determines a first basis pattern 310 and performs spatial shift modulation horizontally with respect to the first pattern to obtain shift patterns 320 to 340 for the first basis pattern 310.

The first shift pattern is marked as $B_1^1$, has moved by 0 in the x axis (horizontal direction) and by 0 in the y axis (vertical direction) based on the first basis pattern 310, B1, and is the same as the first basis pattern 310. The second shift pattern 320 of the first basis pattern 310 is marked as $B_2^1$ and has shifted by 1 in the x axis (horizontal direction) and by 0 in the y axis (vertical direction) based on the first basis pattern 310, B1. The third shift pattern 330 of the first basis pattern 310 is marked as $B_3^1$ and has shifted by 2 in the x axis (horizontal direction) and by 0 in the y axis (vertical direction) based on the first basis pattern 310, B1. The modulation controller 130 of FIG. 3A performs spatial shift modulation, for instance, nine times horizontally by 1 on the basis of the first basis pattern 310 to obtain ten shift patterns. The last shift pattern of the first basis pattern 310, that is, a tenth pattern 340, is marked as $B_{10}^1$ and has shifted by 9 in the x axis (horizontal direction) and by 0 in the y axis (vertical direction) based on the first basis pattern 310, B1.

The modulation controller 130 may also perform spatial shift modulation in the vertical direction on the first basis pattern 310. In one example, the modulation controller 130 may perform spatial shift modulation nine times vertically by 1 on each of the ten shift patterns that have been obtained through horizontal spatial shift modulation to obtain a total of one hundred shift patterns including the basis pattern 310.

The modulation controller 130 may sequentially apply the total of one hundred shift patterns to the spatial light modulator 120 and the image generator 150 generates tomography images for each of the shift patterns.

The tomography image generating apparatus 100 may perform spatial shift modulation, as described above, on other basis patterns aside the first basis pattern 310 to obtain shift patterns for each basis pattern. The tomography image generating apparatus 100 may further apply each basis pattern and each of the shift patterns for each basis pattern to the spatial light modulator 120 to generate tomography images.

FIG. 3B is illustrating an example of operations to obtain the plurality of shift patterns from the modulation controller in FIG. 1 performing spatial shift modulation on the basis pattern, according to an embodiment. Referring to FIG. 3B, the modulation controller shifts the arrangement of pixels vertically or horizontally by a predetermined number with respect to the basis pattern. The predetermined number may vary from at least 1 to higher numbers. For the convenience of description, the spatial light modulator 120 of FIG. 3B is described below as a digital micromirror device (DMD). The DMD includes micro-mirrors reflecting incident rays, controls an on/off operation of each of the micro-mirrors, and forms patterns according to the arrangement of the on/off pixels. For the convenience of description, it is assumed below that a black color is on and a white color is off. However, the on/off colors may be the opposite ones.

The spatial light modulator 120 performs spatial shift modulation on a basis pattern to shift the on/off arrangement of the pixels by a given number vertically or horizontally, with respect to one basis pattern that is formed by the on/off arrangement of pixels. In one illustrative configuration, although the spatial shift modulation is illustrated as shifting the basis pattern vertically by the predetermined number of 1, it is not limited thereto.

Referring to FIG. 3B, for a first basis pattern 350, the pixels of the leftmost column in the on/off arrangement are all in an off state, except for the fourth pixel from the top. When looking into a first shift pattern 360, which is spatial shift modulated vertically by 1 with respect to the first basis pattern 350, one of the pixels that is fifth from the top in the leftmost column turns on. When looking into a fourth shift pattern 370 that is spatial shift modulated vertically by 4 with respect to the first basis pattern 350, one of the pixels that is third from the top in the leftmost column turns on.

As described above, the modulation controller 130 may sequentially shift vertically or horizontally the on/off arrangement of the pixels of the spatial light modulator based on one basis pattern to perform spatial shift modulation.

Figure 4:
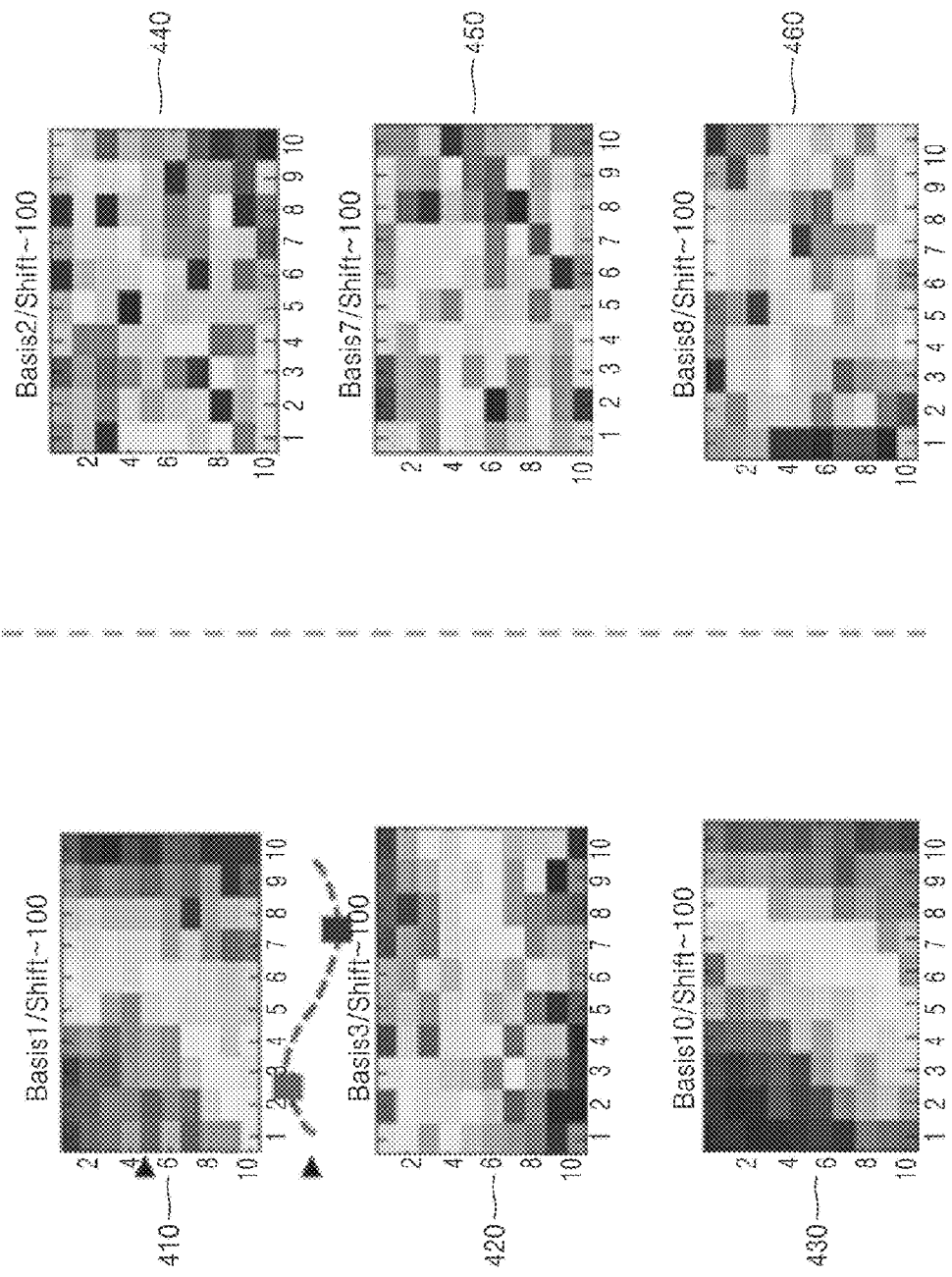
FIG. 4 is illustrating an example of operations to select phase shift spectrum images that show regular phase shift among the phase shift spectrum images generated by an image processor illustrated in FIG. 1, according to an embodiment.

FIG. 4 is illustrating an example of operations to select phase shift spectrum images that show regular phase shift among the phase shift spectrum images generated by an image processing unit illustrated in FIG. 1, according to an embodiment. The phase modulation spectrum images illustrated in FIG. 4 include the spectrum images of one hundred shift patterns that are obtained by performing spatial shift modulation ninety-nine times on each basis pattern.

Although FIG. 4 illustrates six spectrum images that are some of phase modulation spectrum images for ten basis patterns in total, a person of ordinary skill in the relevant art will appreciate that less or more spectrum images may be illustrated.

The image generator 150 obtains spectrum images for each basis pattern and shift patterns based on the spectrum signals that are obtained from the detector 140. The image processor 160 arranges the spectrum images of the shift patterns of each basis pattern in matrix form according to the shift direction and shift amount of spatial shift modulation. The image processor 160 generates phase shift spectrum images for each basis pattern. A phase shift spectrum image represents the phase shift of the rays according to the spatial shift modulation of a basis pattern and shift patterns of the basis pattern. The spectrum images of one hundred shift patterns are arranged in each phase shift spectrum image as illustrated in FIG. 4 in matrix form, according to a shift direction and a shift amount.

A phase shift spectrum image 410 of a first basis pattern (Basis 1) shows regular phase shift according to spatial shift modulation. In one illustrative example, the phase shift spectrum image 410 represents phase shift with sinusoidal characteristics. A phase shift spectrum image 420 of a third basis pattern (Basis 3) has less regular phase shift compared to the phase shift spectrum image 410, but represents phase shift with sinusoidal characteristics compared to the phase shift spectrum images 440 to 460 on the right side. The phase shift spectrum image 430 of a tenth basis pattern (Basis 10) also shows regular phase shift according to spatial shift modulation.

On the other hand, a phase shift spectrum image 440 of a second basis pattern (Basis 2) represents irregular phase shift according to spatial shift modulation. The other phase shift spectrum images 450 and 460 also represent irregular phase shift according to spatial shift modulation and do not represent sinusoidal characteristics.

The image processor 160 may use the basis patterns of phase shift spectrum images 410 to 430, which show regular phase shift among phase shift spectrum images 410 to 460, and the shift patterns of the basis pattern to generate the final pattern. For instance, the modulation controller 130 applies the Basis 1, the Basis 3, and the Basis 10 of phase shift spectrum images 410 to 430 representing regular phase shift, and the one hundred shift patterns of the basis patterns to the spatial light modulator 120. Thus, the image generator 150 generates tomography images for each of the Basis 1, the Basis 3, the Basis 10, and the one hundred shift patterns of the basis patterns, that is, the Basis 1, the Basis 3 and the Basis 10. The image generator 160 selects one pattern that generates a clearest tomography image among each of the Basis 1, the Basis 3, and the Basis 10, and shift patterns of the basis patterns.

As described above, in one illustrative example, the tomography image generating apparatus 100 uses the basis patterns of the phase shift spectrum images representing regular phase shift and the shift patterns of the basis patterns to generate the final pattern.

Figure 5:
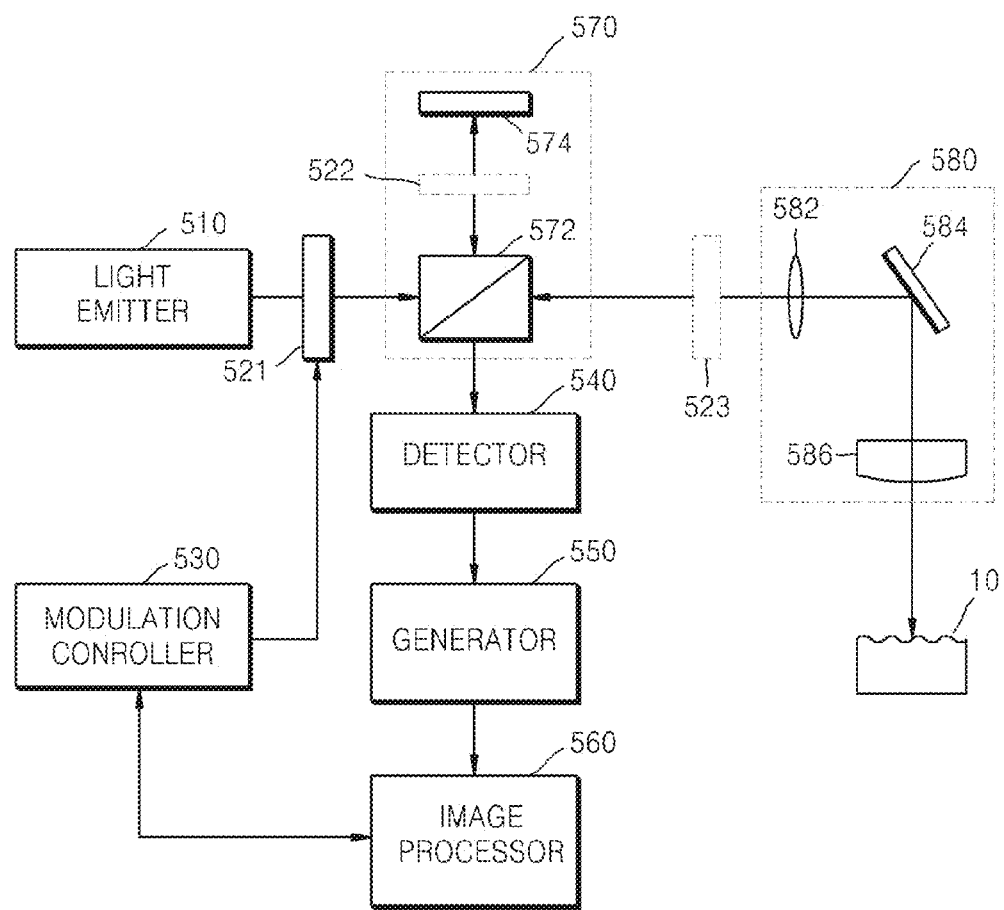
FIG. 5 is illustrating an optical coherence tomography apparatus corresponding to the apparatus to generate tomography images illustrated in FIG. 1, according to an embodiment.

FIG. 5 is illustrating an optical coherence tomography apparatus corresponding to the apparatus to generate tomography images illustrated in FIG. 1, according to an embodiment. Referring to FIG. 5, the optical coherence tomography apparatus 500 includes a light emitter 510, a spatial light modulator 521, a modulation controller 530, a detector 540, an image generator 550, an image processor 560, an interferometer 570, and an optical probe 580. The descriptions presented above with regards to FIG. 1 and in relation to the light emitter 110, the spatial light modulator 120, the modulation controller 130, the detector 140, the image generator 150, and the image processor 160 may be applicable to the light emitter 510, the spatial light modulator 521, the modulation controller 530, the detector 540, the image generator 550, and the image processor 560 illustrated in FIG. 5, thus the detailed descriptions related to these structural devices are not repeated. Furthermore, the descriptions made above in relation to the tomography image generating apparatus 100 illustrated FIGS. 1 to 4 may also apply to the optical coherence tomography apparatus 500 of FIG. 5.

The light emitter 510 emits rays incident upon the subject. In this case, the rays emitted from the light emitter 510 may correspond to wavelength-swept light or laser, but not limited thereto. The light emitter 510 transfers the emitted rays to the interferometer 570. According to one embodiment, the spatial light modulator 521 is located between the light emitter 510 and the interferometer 570. Thus, the rays phase-modulated by the spatial light modulator 521 is transferred to the interferometer 570.

The spatial light modulator 521 modulates the phase of rays according to a pattern in which pixels are arranged. The spatial light modulator 521 of the optical coherence tomography apparatus 500 modulates the phase of any one of a measuring ray, and a reference ray and the rays emitted from the light emitter 510.

Referring to FIG. 5, the spatial light modulator 521 of the optical coherence tomography apparatus 500 may be located at a second location 522 or a third location 523 as well as the location between the light emitter 510 and the interferometer 570. That is, the spatial light modulator 521 may be located at any one location between the light emitter 510 and the interferometer 570, between a reference mirror 574 and a beam splitter 572 of the interferometer 570, and between the beam splitter 572 and a probe 580 at which the measuring ray separated from the beam splitter 572 enters toward the probe 580.

The modulation controller 530 determines at least one basis pattern of the spatial light modulator 521, performs spatial shift modulation shifting the arrangement of pixels by a predetermined number vertically or horizontally with respect to a basis pattern to obtain shift patterns of the basis pattern, and controls the spatial light modulator 521 so that the basis pattern and the shift patterns of the basis pattern are sequentially applied to the spatial light modulator 521.

The interferometer 570 divides the rays emitted from the light emitter 510 into measuring rays and reference rays, directs the measuring rays to the subject 10. The interferometer 570 also receives response rays that are reflection of the measuring rays from the subject 10.

The detector 540 detects interference signals that are generated by the response rays and the reference rays, and detects spectrum signals for a basis pattern and each of shift patterns of the basis pattern based on the interference signals. The detector 540 transfers the detected spectrum signals to the image generator 550.

The image generator 550 uses spectrum signals to generate tomography images for the basis pattern and the shift patterns of the basis pattern.

The image processor 560 selects a pattern that generates the clearest tomography image among the basis pattern and the shift patterns of the basis pattern based on the generated tomography images. The image generator 550 generates the final tomography image of the subject 10 using spectrum signals based on interference signals, which are obtained by applying the selected pattern to the spatial light modulator 521.

The interferometer 570 may include a beam splitter 572 and a reference mirror 574. The rays transferred from the light emitter 510 are split into measuring rays and reference rays at the beam splitter 572. The measuring rays split at the beam splitter 572 are transferred to the optical probe 580. The reference rays are transferred to and reflected from the reference mirror 584 and then the reference rays return to the beam splitter 582. In addition, the measuring rays transferred to the optical probe 580 are directed to the subject 10. An inner tomography image of the subject 10 is captured through the optical probe 580. The response rays, which are reflection of the measuring rays from the subject 10, are transferred to the beam splitter 572 of the interferometer 570 through the optical probe 580. The response rays and the reference rays reflected from the reference mirror 574 cause interference at the beam splitter 572.

The optical probe 580 may include a collimator lens 582, a galvano scanner 584, and a lens 586. In this case, the galvano scanner 584 is a mirror that is possible to rotate through a given range on a certain axis, and may be implemented as a micro electro mechanical system (MEMS) scanner that receives a driving force necessary to rotate. The measuring rays transferred from the interferometer 570 may be collimated through the collimator lens 582 of the optical probe 580 and reflected from the galvano scanner 584 so that a traveling direction of the collimated measuring rays is adjusted and the rays are irradiated to the subject 10 after passing through the lens 586.

Thus, the optical coherence tomography apparatus 500 may select a pattern, which generates the clearest tomography image among shift patterns of a basis pattern obtained through spatial shift modulation. The optical coherence tomography apparatus 500 would obtain a pattern that reflects a phase modulation amount most suitable for the material characteristics of subject 10. The optical coherence tomography apparatus 500 generates, with the obtained pattern, an optimal tomography image with an increased transmission depth.

Figure 6:
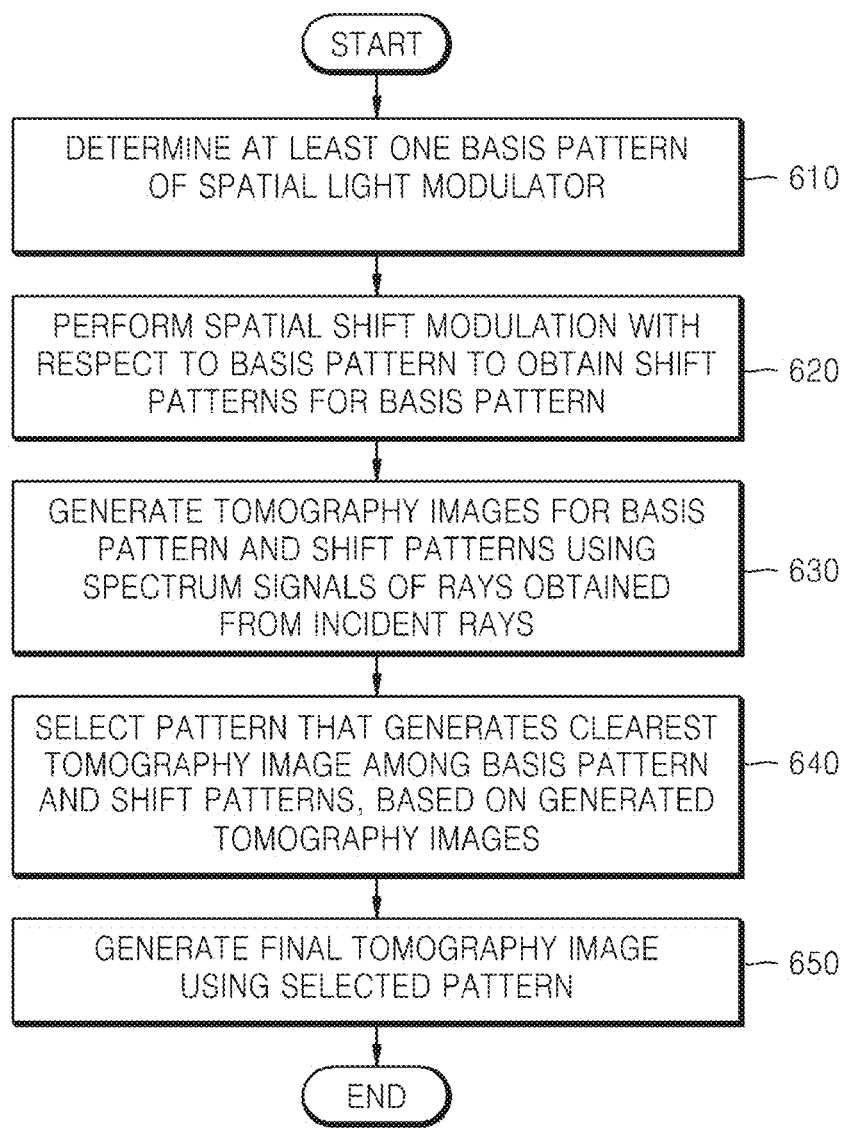
FIG. 6 is a flow chart representing a method to generate tomography images, according to an embodiment.

FIG. 6 is a flow chart representing a method to generate tomography images, according to an embodiment. Referring to FIG. 6, the method illustrated in FIG. 6 includes operations processed at the tomography image generating apparatus 100 or the optical coherence tomography apparatus 500 illustrated in FIGS. 1 to 5. Thus, as may be appreciated, the descriptions made above in relation to the tomography image generating apparatus 100 or the optical coherence tomography apparatus 500 illustrated in FIGS. 1 to 5 may be applied to the method illustrated in FIG. 6.

At operation 610, the modulation controller 130 determines at least one basis pattern of the spatial light modulator 120 that modulates the phases of incident rays according to a pattern in which pixels are arranged. At operation 620, the modulation controller 130 performs spatial shift modulation that shifts the arrangement of the pixels by a predetermined number vertically or horizontally with respect to a basis pattern to obtain shift patterns of the basis pattern. At operation 630, the image generator 150 generates tomography images for the basis pattern and the shift patterns of the basis pattern using the spectrum signals of rays that are obtained by the rays passing through the spatial light modulator 120 and entering the subject 10.

At operation 640, the image processor 160 selects a pattern that generates the clearest tomography image among the basis pattern and the shift patterns of the basis pattern based on the generated tomography images.

In step 650, the image generator 150 generates the final tomography image for the subject 10 using the selected pattern.

Figure 7:
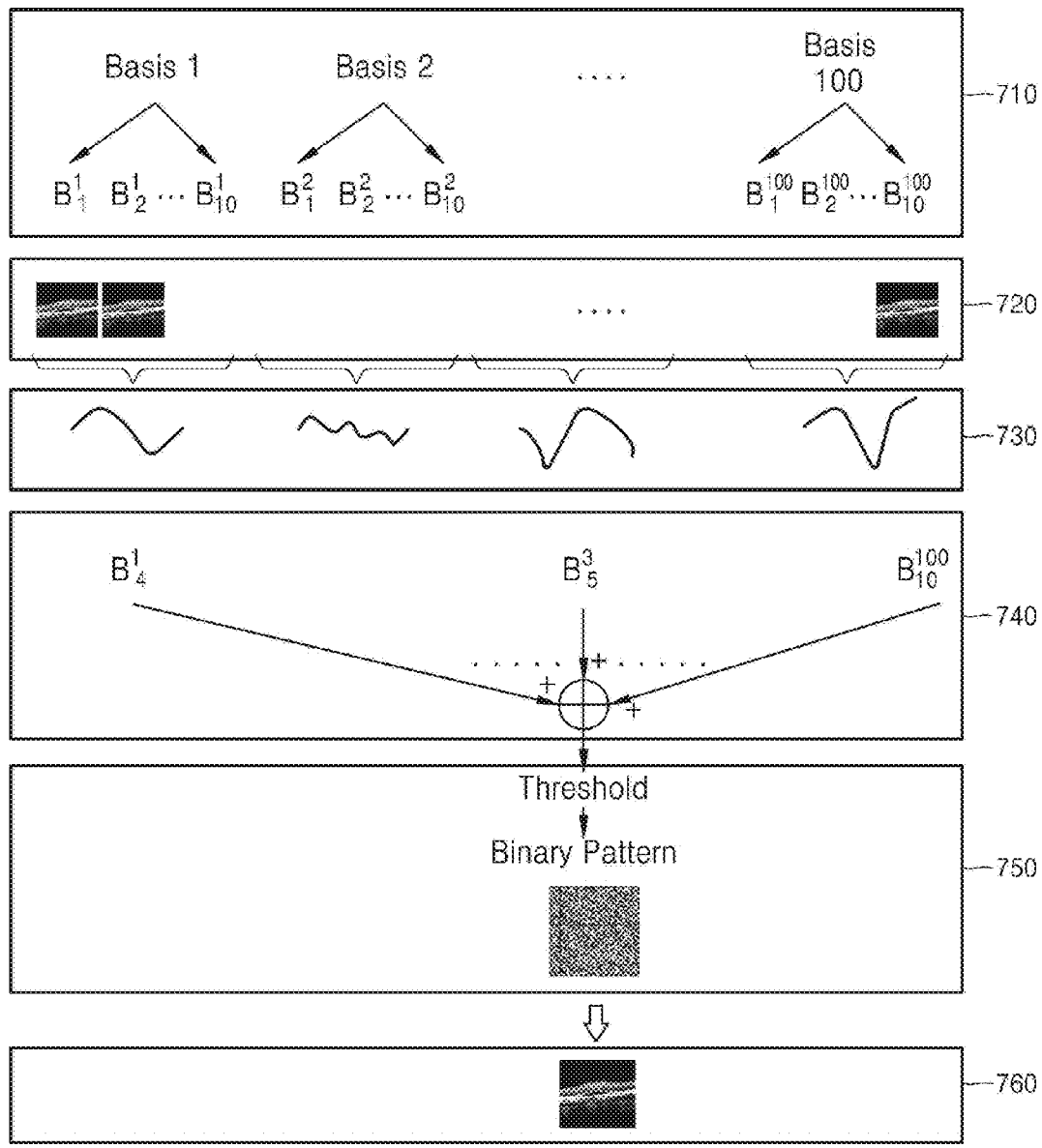
FIG. 7 is a flow chart representing a method to generate tomography images, according to another embodiment.

FIG. 7 is a flow chart representing a method to generate tomography images, according to another embodiment. Referring to FIG. 7, the method illustrated in FIG. 7 includes operations processed at the tomography image generating apparatus 100 or the optical coherence tomography apparatus 500 illustrated in FIGS. 1 to 5. Thus, as may be appreciated, the descriptions made above in relation to the tomography image generating apparatus 100 or the optical coherence tomography apparatus 500 illustrated in FIGS. 1 to 5 may be applied to the method illustrated in FIG. 7.

At operation 710, the modulation controller 130 determines basis patterns of the spatial light modulator 120 that modulates the phases of incident rays according to a pattern in which pixels are arranged. The modulation controller 130 performs spatial shift modulation that shifts the arrangement of the pixels by a predetermined number vertically or horizontally with respect to each basis pattern to obtain shift patterns for each basis pattern.

In this case, the basis patterns for a subject 10 are uncorrelated with each other in the phase modulation of rays according to the spatial shift modulation. For example, a basis pattern B1, a basis pattern B2, and a basis pattern B100 are uncorrelated with one another and do not affect the phase modulation according to the spatial shift modulation performed on each basis pattern.

At operation 720, the image processor 160 generates tomography images for the basis pattern and shift patterns of the basis pattern using the spectrum signals of rays, which are obtained from the rays passing through the spatial light modulator 120 and entering the subject 10. The image processor 160 selects a pattern that generates the clearest tomography images among each basis pattern and the shift patterns for each basis pattern, on the basis of the generated tomography images. The tomography image generating apparatus 100 repeats, for each basis pattern, the operation of selecting a pattern that generates the clearest tomography image, and obtains selected patterns.

At operation 730, the image processor 160 generates phase shift spectrum images for each basis pattern using the spectrum images of each basis pattern and shift patterns for each basis pattern and selects phase shift spectrum images that show regular phase shift among the generated phase shift spectrum images. The graphs illustrated in operation 730 represent the phase shift of a phase shift spectrum image for each basis pattern. For example, regular phase shift may be sinusoidal characteristics. At operation 730, the phase shift of phase shift spectrum images for the basis patterns B1, B3, and B100 shows sinusoidal characteristics. Thus, shift patterns for B1, B3, and B100 may be used for generating the final pattern.

The image processor 160 may generate phase shift spectrum images in the following way. The image generator 150 obtains spectrum images for each basis pattern and the shift patterns for each basis pattern based on the spectrum signals. The image processor 160 arranges the spectrum images of the shift patterns of a basis pattern in matrix form. The matrix form is in accord with the shift direction and amount of the spatial shift modulation that are based on the spectrum images of the basis pattern and the shift patterns of the basis pattern. The image processor 160 generates one phase shift spectrum image that represents the phase shift of rays according to spatial shift modulation. The image processor 160 repeats, for each of basis patterns, the operations of obtaining phase shift spectrum images.

According to an embodiment, the operation of selecting one pattern that generates the clearest tomography image among each basis pattern and shift patterns of each basis pattern may performed on basis patterns of phase shift spectrum images that show regular phase shift among phase shift spectrum images. In operation 740, the selected pattern that generates the clearest tomography image for B1, B3 and B100 is $B_4^1$, $B_5^3$, and $B_{10}^{100}$, respectively.

At operation 740, the image processor 160 sums the selected patterns as a summation pattern. Referring to FIG. 7, the patterns of $B_4^1$, $B_5^3$, and $B_{10}^{100}$ are summed to generate one summation pattern.

In step 750, the image processor 160 forms the final pattern that is obtained by binarizing the summation pattern on the basis of a predetermined threshold.

At operation 760, the image generator 150 uses the final pattern to generate the final tomography image for the subject 10.

By using the method of generating tomography images described above, it is possible to generate optimal tomography images with an increased transmission depth by adjusting a phase modulation amount to be most suitable for the material characteristics of a subject.

The phase modulation amount most suitable for the material characteristics of the subject may be determined by selecting a pattern generating the clearest tomography images among shift patterns that are obtained by performing spatial shift modulation on a basis pattern.

Meanwhile, program instructions to perform the methods of FIGS. 6 and 7 described above, or one or more operations thereof, may be recorded, stored, or fixed in one or more computer-readable storage media. The program instructions may be implemented by a computer. For example, the computer may cause a processor to execute the program instructions. The media may include, alone or in combination with the program instructions, data files, data structures, and the like. Examples of computer-readable media include magnetic media, such as hard disks, floppy disks, and magnetic tape; optical media such as CD ROM disks and DVDs; magneto-optical media, such as optical disks; and hardware devices that are specially configured to store and perform program instructions, such as read-only memory (ROM), random access memory (RAM), flash memory, and the like. Examples of program instructions include machine code, such as produced by a compiler, and files containing higher level code that may be executed by the computer using an interpreter. The program instructions, that is, software, may be distributed over network coupled computer systems so that the software is stored and executed in a distributed fashion. For example, the software and data may be stored by one or more computer readable recording mediums. Also, functional programs, codes, and code segments for accomplishing the example embodiments disclosed herein can be easily construed by programmers skilled in the art to which the embodiments pertain based on and using the flow diagrams and block diagrams of the figures and their corresponding descriptions as provided herein.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A method to generate a tomography image, the method comprising:
   determining a basis pattern from modulated phases of incident rays from a spatial light modulator according to a pattern of arranged pixels;
   performing spatial shift modulation by deliverately shifting the basis pattern vertically or horizontally to obtain shift patterns of the basis pattern;
   generating tomography images for the basis pattern and the shift patterns using spectrum signals of rays obtained from the incident rays passing through the spatial light modulator and entering a subject; and
   selecting a pattern that generates a clearest tomography image of the subject, which has a greatest light intensity among the generated tomography images, among the basis pattern and the shift patterns.

2. The method of claim 1, further comprising:
   configuring the spatial light modulator to comprise basis patterns for the subject, wherein the basis patterns are uncorrelated with each other in phase modulation of the incident rays according to the spatial shift modulation.

3. The method of claim 2, further comprising:
   determining the basis patterns based on a permutation of a Hadamard pattern.

4. The method of claim 1, further comprising:
   generating a final tomography image for the subject using the selected pattern; and
   configuring the spatial light modulator to comprise basis patterns of the subject,
   wherein the selecting of the pattern comprises
      obtaining selected patterns by repeating, for each of the basis patterns, the selecting of the pattern that generates the clearest tomography image among each basis pattern and the shift patterns;
      summing the selected patterns as a summation pattern; and
      forming a final pattern obtained by binarizing the summation pattern based on a threshold, and
   wherein the generating of the final tomography image comprises generating the final tomography image for the subject using the final pattern.

5. The method of claim 4, further comprising:
   obtaining spectrum images, the spectrum images comprising a spectrum image for the basis pattern and for each of the shift patterns of the basis pattern, based on the spectrum signals; and
   generating a phase shift spectrum image representing phase shift of the obtained rays according to the spatial shift modulation by arranging, in a matrix form, the spectrum images according to a shift direction and a shift amount of the spatial shift modulation based on the spectrum image of the basis pattern,
   wherein the obtaining of the spectrum images and the generating of the phase shift spectrum image are repeated for each of the basis patterns to obtain phase shift spectrum images, and
   wherein the generating of the final pattern comprises generating the final pattern by the selecting of the pattern that generates the clearest tomography image, on the basis patterns of the phase shift spectrum images that have regular phase shift among the phase shift spectrum images.

6. The method of claim 5, further comprising:
   representing the regular phase shift with sinusoidal characteristics.

7. The method of claim 1, further comprising:
   generating a final tomography image for the subject using the selected pattern; and
   determining a region of interest (ROI) that corresponds to a desired transmission depth of the subject to focus the incident rays, wherein the determining of the basis pattern, the performing, the generating, and the selecting are repeated for the ROI to generate the final tomography image for the ROI.

8. The method of claim 7, wherein the determining of the ROI comprises
   determining the desired transmission depth of the subject to focus the incident rays based on an intensity of the spectrum signals according to transmission depth of the subject, and
   determining a region corresponding to the desired transmission depth as the ROI.

9. The method of claim 1, further comprising:
   determining regions of interest (ROIs) that have different transmission depths of the subject to focus the incident rays, wherein the determining of the basis pattern, the performing, the generating, and the selecting are repeated for each of the ROIs to generate final tomography images, and the final tomography images are combined to generate an edited tomography image.

10. The method of claim 1, further comprising:
    horizontally moving the incident rays on the subject,
    obtaining final tomography images by repeating the determining of the basis pattern, the performing, the generating, and the selecting, in response to moving the incident rays horizontally,
    generating the tomography image, the tomography image comprising a region that corresponds to a moving distance on the subject using the final tomography images.

11. The method of claim 1, further comprising:
    configuring the spatial light modulator to be a digital micro-mirror device (DMD).

12. The method of claim 1, further comprising:
    performing the determining, the performing, the generating, and the selecting at an optical coherent tomography (OCT) apparatus or an optical coherent microscopy (OCM) apparatus.

13. A non-transitory computer readable storage medium containing a computer program configured to control a processor to perform the method of claim 1.

* * * * *